United States Patent

Whitehorse-Burns

Patent Number: 5,996,928
Date of Patent: Dec. 7, 1999

[54] DENTAL FLOSS DISPENSER

[76] Inventor: Ruth Ann Whitehorse-Burns, 5607 Chestnut La., Mc Farland, Wis. 53558

[21] Appl. No.: 09/174,345

[22] Filed: Oct. 15, 1998

[51] Int. Cl.⁶ ............................. B65H 16/10; B26F 3/02
[52] U.S. Cl. ..................... 242/564.2; 225/16; 225/34; 225/38; 312/237; 206/63.5; 132/324
[58] Field of Search ............................. 242/564.2, 564.1, 242/565, 594.5; 225/16, 11, 38, 34; 312/34.19, 237; 206/63.5; 132/324, 325, 314, 308, 309, 310

[56] References Cited

U.S. PATENT DOCUMENTS

| | | |
|---|---|---|
| D. 306,500 | 3/1990 | Brahler . |
| 1,092,743 | 4/1914 | Parvin et al. . |
| 2,865,699 | 12/1958 | Fitzgerald ................................. 225/11 |
| 3,107,957 | 10/1963 | Batlas et al. . |
| 3,168,230 | 2/1965 | Fahrenbach . |
| 3,894,550 | 7/1975 | Eaton . |
| 4,844,104 | 7/1989 | Martin . |
| 5,016,661 | 5/1991 | Israel et al. . |
| 5,160,077 | 11/1992 | Sticklin .................................... 225/38 |
| 5,215,193 | 6/1993 | Dennis . |
| 5,246,022 | 9/1993 | Israel et al. . |
| 5,490,722 | 2/1996 | Sonnett et al. ........................ 312/237 |
| 5,765,739 | 6/1998 | Yates, III . |

*Primary Examiner*—Donald P. Walsh
*Assistant Examiner*—William A. Rivera

[57] ABSTRACT

A dental floss dispenser including a housing with dental floss stored therein. Also included is at least one dental floss dispensing assembly for dispensing a predetermined length of the dental floss from the housing. The dental floss dispensing assembly includes a slider slidably mounted within the housing for dispensing the floss upon being manually slid via a lever.

6 Claims, 2 Drawing Sheets

DENTAL FLOSS DISPENSER

BACKGROUND OF THE INVENTION

1. Field of the Invention

The present invention relates to hand-held dental floss dispensers and more particularly pertains to a new dental floss dispenser for conveniently dispensing a predetermined amount of dental floss.

2. Description of the Prior Art

The use of hand-held dental floss dispensers is known in the prior art. More specifically, hand-held dental floss dispensers heretofore devised and utilized are known to consist basically of familiar, expected and obvious structural configurations, notwithstanding the myriad of designs encompassed by the crowded prior art which have been developed for the fulfillment of countless objectives and requirements.

Known prior art hand-held dental floss dispensers include U. S. Pat. No. 4,844,104; U.S. Pat. No. 5,246,022; U.S. Pat. No. 5,215,193; U.S. Pat. No. 5,016,661; U.S. Pat. Des. 306,500; and U.S. Pat. No. 3,894,550.

In these respects, the dental floss dispenser according to the present invention substantially departs from the conventional concepts and designs of the prior art, and in so doing provides an apparatus primarily developed for the purpose of conveniently dispensing a predetermined amount of dental floss.

SUMMARY OF THE INVENTION

In view of the foregoing disadvantages inherent in the known types of hand-held dental floss dispensers now present in the prior art, the present invention provides a new dental floss dispenser construction wherein the same can be utilized for conveniently dispensing a predetermined amount of dental floss.

The general purpose of the present invention, which will be described subsequently in greater detail, is to provide a new dental floss dispenser apparatus and method which has many of the advantages of the hand-held dental floss dispensers mentioned heretofore and many novel features that result in a new dental floss dispenser which is not anticipated, rendered obvious, suggested, or even implied by any of the prior art hand-held dental floss dispensers, either alone or in any combination thereof.

To attain this, the present invention generally comprises a housing having a rectangular configuration. The housing is equipped with a rear face, a front face and a thin periphery formed therebetween. As shown in FIGS. 1 & 2, the top face of the periphery of the housing is equipped with a rectangular opening formed therein with a lid pivotally mounted thereon. Such lid is adapted for allowing selective access to an interior space of the housing. The front face of the housing also has a plurality of parallel vertically oriented slots formed therein for reasons that will soon become apparent. Further, the bottom face of the housing has a horizontally oriented slot formed therein between side faces of the periphery of the housing, as shown in FIG. 2. Next provided is a plurality of laterally spaced dental floss dispensing assemblies. Each of such assemblies includes a dental floss supporting rod mounted between the side faces of the periphery of the housing adjacent to the opening of the top face. Each dental floss supporting rod is adapted for supporting a spool of dental floss. Also included as a component of each dental floss dispensing assembly are vertically oriented guides having a bottom end mounted on the bottom face of the housing within the interior space thereof below the dental floss supporting rod. A slider block is provided with vertically oriented grooves for slidably receiving the guides, as shown in FIG. 4. With reference now to FIG. 5, the slider block is shown to have an arm mounted on a top of the slider block and extending forwardly therefrom. An aperture is formed in the slider block for passing dental floss from the corresponding spool of dental floss. Each dental floss dispensing assembly further includes an L-shaped lever having a top end pivotally coupled to the arm of the slider block. A bottom end of such lever extends from one of the vertically oriented slots of the housing. In use, the L-shaped lever has a raised orientation and a lowered orientation. As shown in FIG. 5, a pair of elastomeric tabs are coupled to a lower end of the slider block and a lower end of the L-shaped lever for pinching the dental floss when in the lowered orientation. Further, a coil spring is coupled between a top of the front face of the housing and the L-shaped lever. See FIG. 2. In use, the coil spring serves for urging the dental floss dispensing assembly to a top of the housing and the L-shaped lever into the raised orientation. During operation, the L-shaped lever is manually transferred to the lowered orientation thereby pinching the dental floss between the tabs. Thereafter, the dispensing assembly is manually lowered to dispense the dental floss from the horizontally oriented slot. A sharpened edge lining the horizontally oriented slot may be used to sever the dispensed dental floss. As shown in FIG. 1, a coin acceptor is mounted on an upper corner of the front face of the housing for accepting a coin.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental floss dispenser apparatus and method which has many of the advantages of the hand-held dental floss dispensers mentioned heretofore and many novel features that result in a new dental floss dispenser which is not anticipated, rendered obvious, suggested, or even implied by any of the prior art hand-held dental floss dispensers, either alone or in any combination thereof.

It is another object of the present invention to provide a new dental floss dispenser which may be easily and efficiently manufactured and marketed.

It is a further object of the present invention to provide a new dental floss dispenser which is of a durable and reliable construction.

An even further object of the present invention is to provide a new dental floss dispenser which is susceptible of a low cost of manufacture with regard to both materials and labor, and which accordingly is then susceptible of low prices of sale to the consuming public, thereby making such dental floss dispenser economically available to the buying public.

Still yet another object of the present invention is to provide a new dental floss dispenser which provides in the apparatuses and methods of the prior art some of the advantages thereof, while simultaneously overcoming some of the disadvantages normally associated therewith.

Still another object of the present invention is to provide a new dental floss dispenser for conveniently dispensing a predetermined amount of dental floss.

Even still another object of the present invention is to provide a new dental floss dispenser that includes a housing with dental floss stored therein. Also included is at least one dental floss dispensing assembly for dispensing a predetermined length of the dental floss from the housing. The dental floss dispensing assembly includes a slider slidably mounted within the housing for dispensing the floss upon being manually slid via a lever.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figures 1, 2:
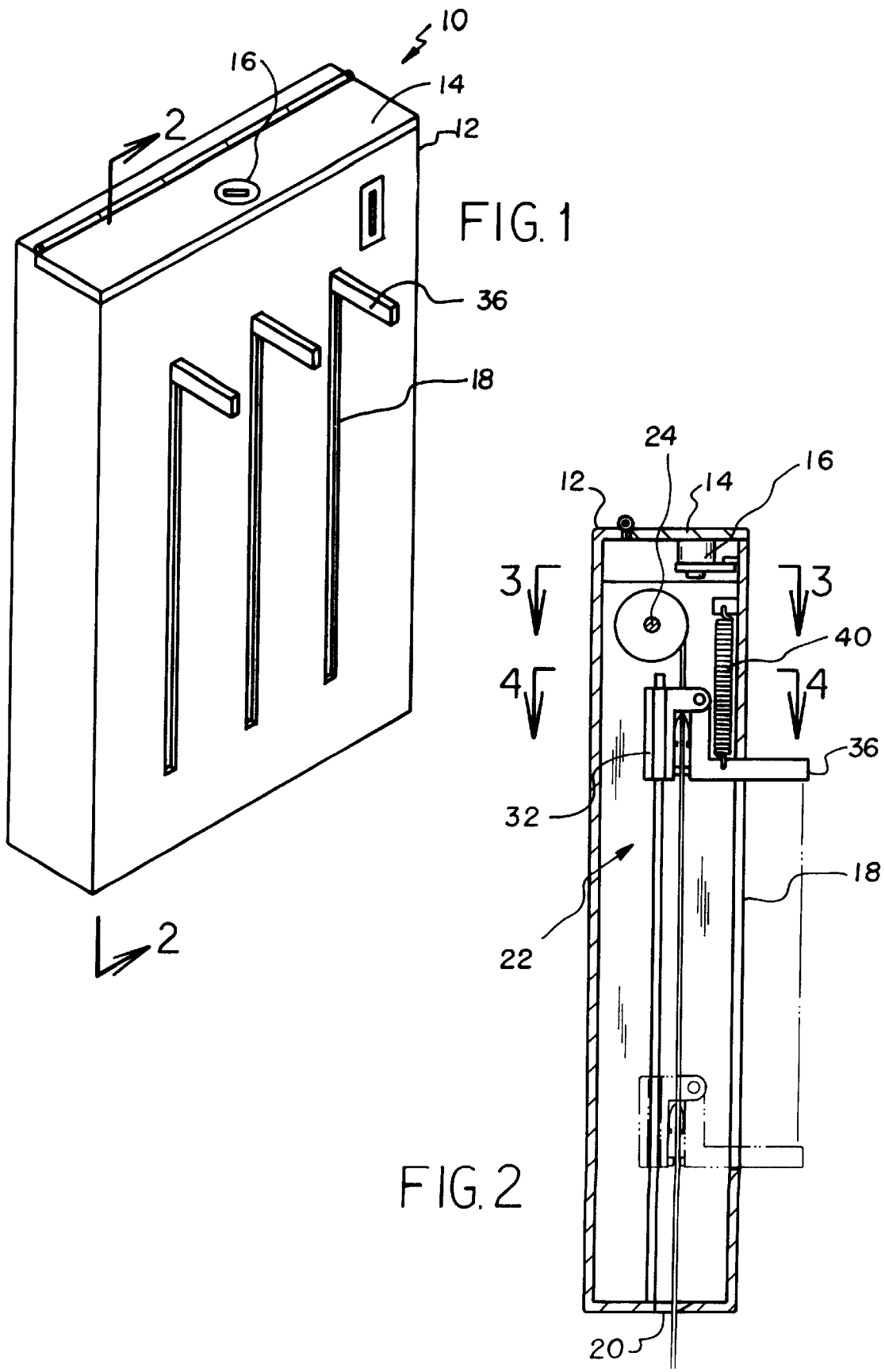
FIG. 1 is a front perspective view of a new dental floss dispenser according to the present invention.
FIG. 2 is a side cross-sectional view of the present invention.
Figure 3:
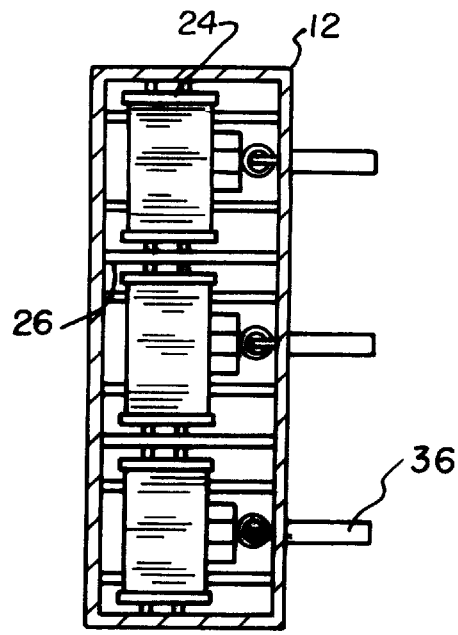
FIG. 3 is a top cross-sectional view of the present invention taken along line 3—3 shown in FIG. 2.

With reference now to the drawings, and in particular to FIGS. 1 through 5 thereof, a new dental floss dispenser embodying the principles and concepts of the present invention and generally designated by the reference numeral 10 will be described.

The present invention, designated as numeral 10, includes a wall-mounted housing 12 having a rectangular configuration. The housing is equipped with a rear face, a front face and a thin periphery formed therebetween. As shown in FIGS. 1 & 2, the top face of the periphery of the housing is equipped with a rectangular opening formed therein with a lid 14 pivotally mounted thereon. Ideally, the lid is equipped with a key actuated lock 16. As such, the lid is adapted for allowing selective access to an interior space of the housing to authorized personnel only. The front face of the housing also has a plurality of parallel vertically oriented slots 18 formed therein for reasons that will soon become apparent. Further, the bottom face of the housing has a horizontally oriented slot 20 formed therein between side faces of the periphery of the housing, as shown in FIG. 2.

Next provided are three laterally spaced dental floss dispensing assemblies 22. Each of such assemblies includes a dental floss supporting rod 24 mounted between the side faces of the periphery of the housing adjacent to the opening of the top face. Each dental floss supporting rod is adapted for supporting a spool of dental floss. Ideally, each dental floss supporting rod is removably mounted from between a plurality of intermediate supports 26 which are mounted between the front and rear face of the housing. This allows convenient replacement of the dental floss when needed. As an option, the floss of each spool includes a unique flavoring.

Figure 4:
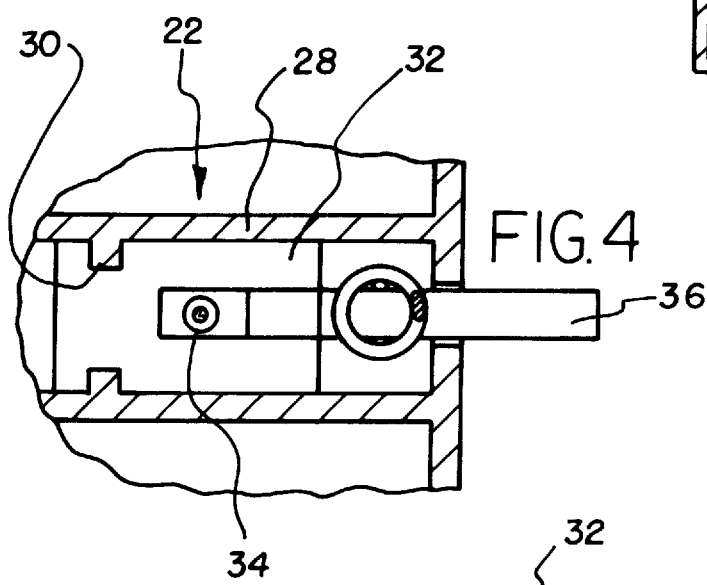
FIG. 4 is a top cross-sectional view of the present invention taken along line 4—4 shown in FIG. 2.
Figure 5:
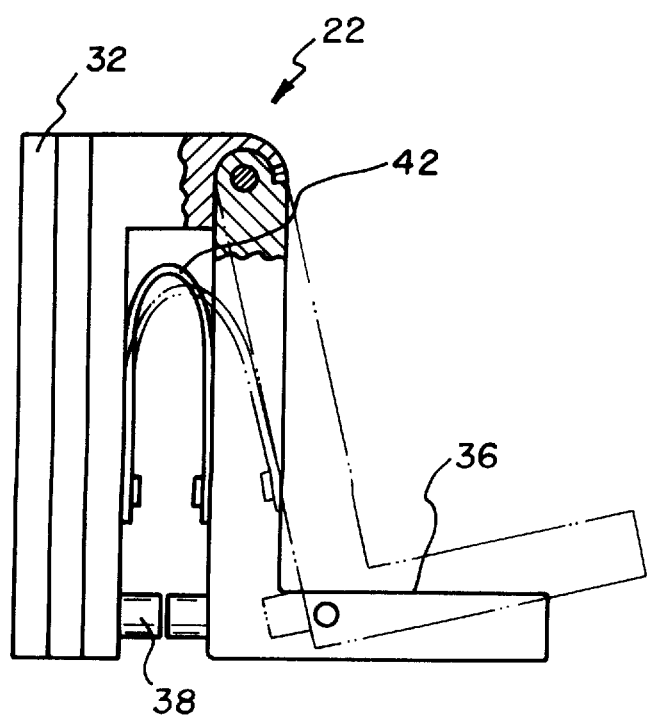
FIG. 5 is a side view of the slider block and lever of one of the dental floss dispensing assemblies of the present invention.

Also included as components of each dental floss dispensing assembly are a pair of vertically oriented guides 28 having a bottom end mounted on the bottom face of the housing within the interior space thereof below the dental floss supporting rod. As shown in FIG. 4, each pair of guides includes walls mounted between the front and rear faces of the housings each with a vertically oriented flange 30 formed thereon. A slider block 32 is provided with vertically oriented grooves for slidably receiving the guides, as shown in FIG. 4. With reference now to FIG. 5, the slider block is shown to have an arm mounted on a top of the slider block and extended forwardly therefrom. It should be noted that an aperture 34 is formed in the slider block for passing dental floss from the corresponding spool of dental floss.

Each dental floss dispensing assembly further includes an L-shaped lever 36 having a top end pivotally coupled to the arm of the slider block. A bottom end of such lever extends from one of the vertically oriented slots of the housing. In use, the L-shaped lever has a raised orientation and a lowered orientation. As shown in FIG. 5, a pair of elastomeric cylindrical tabs 38 are coupled to a lower end of the slider block and a lower end of the L-shaped lever for pinching the dental floss when in the lowered orientation. Further, a coil spring 40 is coupled between a top of the front face of the housing and the L-shaped lever. See FIG. 2. In use, the coil spring serves for urging the dental floss dispensing assembly to a top of the housing and the L-shaped lever into the raised orientation. To further urge the L-shaped lever into the raised orientation, an inverted V-shaped leaf spring is preferably situated between the L-shaped lever and the slider block. As an option, such leaf spring 42 may be equipped with an aperture for passing the dental floss similar to the slider block.

During operation, the L-shaped lever is manually transferred to the lowered orientation thereby pinching the dental floss between the tabs. Thereafter, the dispensing assembly is manually lowered to dispense the dental floss from the horizontally oriented slot. A length of the dispensed dental floss is accordingly about a height of the housing. A sharpened edge lining the horizontally oriented slot may be used to sever the dispensed dental floss. Ideally, the dental floss is automatically severed upon the abutment of the slider block with the blade. As shown in FIG. 1, a coin acceptor may be optionally mounted on an upper corner of the front face of the housing for accepting a coin. As an option, such coin acceptor may include a ratchet mechanism for allowing the rotation of the spools only a predetermined amount when a coin is accepted in order to prevent over dispensing of the dental floss.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A dental floss dispenser comprising, in combination:
   a housing having a rectangular configuration with a rear face, a front face and a thin periphery formed therebetween including a top face with a rectangular opening formed therein with a lid pivotally mounted thereon for allowing selective access to an interior space of the housing, the front face of the housing having a plurality of parallel vertically oriented slots formed therein, the bottom face having a horizontally oriented slot formed therein between side faces of the periphery of the housing;
   a plurality of laterally spaced dental floss dispensing assemblies each including a dental floss supporting rod mounted between the side faces of the periphery of the housing adjacent to the opening of the top face for supporting a spool of dental floss, vertically mounted guides having a bottom end mounted on the bottom face of the housing within the interior space thereof below the dental floss supporting rod, a slider block having vertically oriented grooves for slidably moving along the guides and an arm mounted on a top of the slider block and extending forwardly therefrom with an aperture formed therein for passing dental floss from the corresponding spool of dental floss, an L-shaped lever having a top end pivotally coupled to the arm of the slider block and a bottom end extending from one of the vertically oriented slots of the housing wherein the L-shaped lever has a raised orientation and a lowered orientation, a pair of elastomeric tabs coupled to a lower end of the slider block and a lower end of the L-shaped lever for pinching the dental floss when in the lowered orientation, and a coil spring coupled between a top of the front face of the housing and the L-shaped lever for urging the dental floss dispensing assembly to a top of the housing and the L-shaped lever into the raised orientation;
   wherein the L-shaped lever may be transferred to the lowered orientation thereby pinching the dental floss after which the dispensing assembly may be manually lowered to dispense the dental floss from the horizontally oriented slot; and
   a coin acceptor mounted on an upper corner of the front face of the housing for accepting a coin.

2. A dental floss dispenser comprising:
   a housing with a spool of dental floss stored therein; and
   at least one dental floss dispensing assembly for dispensing a predetermined length of the dental floss from the housing;
   wherein the dental floss dispensing assembly includes a a slider block having an arm mounted on a top of the slider block and extending therefrom with an aperture formed therein for passing dental floss from the corresponding spool of dental floss, an L-shaped lever having a top end pivotally coupled to the arm of the slider block and bottom end extending from the housing, the L-shaped lever has a raised orientation and lowered orientation wherein the L-shaped lever may be transferred to the lowered orientation thereby pinching the dental floss after which the dispensing assembly may be manually lowered to dispense the dental floss.

3. A dental floss dispenser as set forth in claim 2 and further including a money acceptor mounted on the housing for accepting money.

4. A dental floss dispenser as set forth in claim 2 wherein the dental floss dispensing assembly includes a spring for urging the spring into an unbiased orientation.

5. A dental floss dispenser comprising:
   a housing with a spool of dental floss stored therein;
   said housing having a front face, a back face, a top and a bottom, the front face of the housing having at least one vertically orientated slot therein; and
   at least one dental floss dispensing assembly for dispensing a predetermined length of the dental floss from the housing;
   wherein the dental floss dispensing assembly includes a slider slidably mounted within the housing for dispensing the floss upon being slid, said slider block having an arm mounted on a top of the slider block and extending therefrom with an aperture formed therein for passing dental floss from the corresponding spool of dental floss, an L-shaped lever having a top end pivotally coupled to the arm of the slider block and bottom end extending from one of said vertical orientated slots in the housing, the L-shaped lever has a raised orientation and lowered orientation, a coil spring coupled in between the housing and the L-shaped lever for urging the dental floss dispensing assembly to a top of the housing, wherein the L-shaped lever may be transferred to the lowered orientation thereby pinching the dental floss after which the dispensing assembly may be manually lowered to dispense the dental floss.

6. A dental floss dispenser as set forth in claim 5 and further including a money acceptor mounted on the housing for accepting money.

* * * * *